United States Patent [19]

Tamm

[11] 4,272,508

[45] Jun. 9, 1981

[54] COSMETICS FOR TREATMENT OF HAIR AND SKIN

[76] Inventor: Jurgen Tamm, Martinistrasse 52, 2000 Hamburg 20, Fed. Rep. of Germany

[21] Appl. No.: 25,578

[22] Filed: Mar. 30, 1979

[51] Int. Cl.³ .............................................. A61K 31/56
[52] U.S. Cl. ...................................... 424/45; 424/243
[58] Field of Search ............................ 424/243, 45, 47

[56] References Cited

U.S. PATENT DOCUMENTS

| | | | |
|---|---|---|---|
| 2,943,978 | 7/1960 | Sareh | 424/243 X |
| 4,017,615 | 4/1977 | Shastri et al. | 424/241 |
| 4,039,669 | 8/1977 | Beyler et al. | 424/243 |
| 4,078,061 | 3/1978 | Benson et al. | 424/242 |

FOREIGN PATENT DOCUMENTS 907524  8/1972  Canada.

OTHER PUBLICATIONS

Chemical Abstracts–8th Coll Index, p. 253 1967–1971.

*Primary Examiner*—Leonard Schenkman
*Attorney, Agent, or Firm*—Roylance, Abrams, Berdo & Farley

[57] ABSTRACT

There is disclosed a cosmetic hair or skin composition comprising as an active ingredient 11-α-hydroxyprogesterone and/or a pharmaceutically compatible ester thereof in a pharmaceutically acceptable carrier. There is also disclosed a method for the treatment of individuals exhibiting acne, excessively greasy hair and/or androgenic alopecia, which comprises topically treating the affected area with such composition.

18 Claims, No Drawings

COSMETICS FOR TREATMENT OF HAIR AND SKIN

This invention relates to a preparation useful in the treatment of hair and skin. More particularly, this invention relates to such a preparation which is eminently suited for achieving and preserving good growth of the hair and a healthy, well-cared for skin, especially the scalp.

It has long been known that cosmetic difficulties of the hair and the skin are often due to a shift in the equilibrium of hormones in the body. In order to eliminate such problems, such as excessive loss of the hair or the occurrence of acne, it has been proposed to treat the condition by the use of cosmetic preparations containing certain hormones and/or vitamins. It has been found that a number of natural and synthetic female sex hormones, such as estrone, estradiol and stilbestrol, are similar to one another in their hormonal effect and in their effect on skin tissue, and it has been proposed to use sex hormones cosmetically. For example, the treatment of aging skin with a cream containing a hormone such as estrogen results in a fresh appearance with a rejuvenating effect.

Estrogenes and estrogen containing extracts have been used in biological hair tonics since it was assumed that these female sex hormones would stimulate the growth of hair. Since men suffer from loss of hair more frequently than do women, it follows that such preparations are used mostly by men. However, problems arise when such preparations are used by men. As is well known, hormones are effective in exceedingly small quantities and they are active or effective not only locally at the place on which they are applied but penetrate into the deeper layers of the skin where they enter the circulatory system. Even a very small quantity of a hormone in the blood stream is capable of producing profound physical and mental effects. Thus, the possibility that a hormone contained in a cosmetic preparation may cause some undesirable systemic effect gives rise to a disadvantage which considerably limits the use of such compounds in cosmetic preparations.

In order to avoid the disadvantages inherent in the use of cosmetic preparations containing female sex hormones, a search was made for substances which would have the desired cosmetic effects and which would have very slight hormonic effect. Progesterone and a number of similar steroids which are chemically related to the estrogens have become known as such active substances. However, they also have an effect as sex hormones which greatly limits their use in cosmetic preparations.

It has also been known that the androgenically conditioned cosmetic disturbances, for example, androgenic alopecia, are caused by the male generative gland hormone testosterone. Thus, the loss of hair in the area of the forelock and hair on the top of the head goes hand in hand with the attainment of a certain critical level of the testosterone concentration in the blood. In the case of females, relatively small excesses of testosterone in the blood stream frequently suffice to triger an excessive growth of hair, particularly facial hair (hirsutism).

The contrary effects of testosterone, namely, the promotion of the loss of hair in the area of the forelock and on the top of the head on the one hand, and on the other hand the promotion of the growth of facial hair are based on the same mechanics. These mechanics have been clarified and experiments have been made in order to decrease or eliminate the disadvantages of using testosterone by a corresponding influence on the mechanics. Thus, for example, the hormone of the yellow corpuscles was used in order to impede the effect of the enzyme 5-α-reductase, by which testosterone is reduced in the cell to dihydrotestosterone. Dihydrotestosterone is clearly more effective than testosterone and is coupled with a specific albumin particle (receptor). This complex is transported into the cell nucleus where it may act on the genetic code. Therefore, an attempt has also been made to stop the formation of the receptor complex using cyproteron acetate. The use of a local application of progesterone results in an abatement of the loss of hair in men with androgenic alopecia. However, the use of such active substances in purely cosmetic preparations is still accompanied by problems since these substances have a hormone-effect of their own, or are unsatisfactory, since they are not totally effective locally.

It is an object of this invention to create a cosmetic agent for hair and skin care which may be used locally, which is effective in combatting the previously discussed cosmetic problems, and the active substance of which has no hormone effect and shows no undesirable side effects, even when used for prolonged periods of time.

In accordance with the practice of this invention, it has been found that this object may be attained by providing a cosmetic hair and skin preparation which is characterized by a content of 11-α-hydroxyprogesterone and/or one of its pharmaceutically active and compatible esters. The active substance may be mixed with additives customarily used in hair and skin preparations.

The active substance used in the practice of this invention, 11-α-hydroxyprogesterone, is a known compound. It was produced synthetically as early as 1952 and shows a negligible hormonic effect with large doses in animal experiments, see Proc. Soc. Exper. Biol. & Med. 82, (1953), pp. 243–247. This compound does not occur in humans and has a special inhibiting effect against the 5-α-reductase of testosterone. The 11-α-hydroxyprogesterone used in accordance with this invention and its pharmaceutically effective and compatible esters are eminently suited for the treatment of the previously discussed cosmetic disorders. These preparations have the simultaneous advantages of showing no hormonic or other undesirable side effects so that they may be freely used in cosmetic preparations and are suitable for topical application and care of the hair and scalp whereby they will cause after a relatively brief treatment time (8 to 12 days) a considerable reduction of the greasiness in overly greasy hair, and, after a correspondingly longer application, a clear decrease in the loss of hair. Further, in the case of treatment of acne, a decrease and in many cases a disappearance of the acne symptoms will be achieved after a remarkably short time of treatment.

The advantageous cosmetic effects of 11-α-hydroxyprogesterone in the treatment of local hair disorders, such as androgenic alopecia and excessively greasy hair as well as acne vulgaris, were illustrated by clinical experiments on men and women of 16 to 54 years of age, extending over several months.

For example, 10 men who suffered from excessively greasy hair and loss of hair on the top of the head, were treated locally over a period of 4 to 6 months with a 1% solution of 11-α-hydroxyprogesterone in a 60% ethanol solution. About 10 to 15 ml. of the solution were massaged daily into the scalp. All patients without exception felt a considerable reduction in the annoying greasiness of the hair 8 to 12 days following the beginning of treatment. After about 5 to 6 weeks of treatment, a clear decrease in the loss of hair was observed, and further treatment completely normalized hair retention. During the entire treatment, no side effects were observed.

In an additional experiment, 14 women who suffered from excessive greasiness of the hair and/or from androgenic alopecia submitted to the above-described treatment. The first advantageous effects in the form of a clear reduction of the greasiness of the hair occurred after 8 to 12 days in the case of 12 persons submitting to the experiments and after 5 to 6 weeks, a clear decrease in the loss of hair was found. A few of the individuals undergoing this treatment experienced dryness of the hair which they found to be unpleasant. This difficulty may be overcome by the addition to the preparation of certain skin care additives and/or further decrease of the alcohol content, or by use of another suitable alcohol, for example, isopropanol. The occurrence of unpleasant dryness generally occurs only occasionally in persons having a particularly sensitive skin and/or scalp. Aside from this dryness, no side effects in the treatment of these women of a local or general nature were observed during the treatment.

In a further test, 5 women and 4 men were treated for acne vulgaris of the face and the upper trunk of the body with a specific night cream which contained about 1.4% by weight of 11-α-hydroxyprogesterone in a customary fatty oil-in-water emulsion. This cream was rubbed onto the affected parts of the skin once daily. A noticeable reduction in the acne-efflorescences was observed in all cases after 8 to 10 days. Continued local treatment for about 15 to 20 days produced a lasting improvement of the disease. No local or general side effects were found during and after the treatment.

In experiments similar to those described above, the acetic acid ester of 11-α-hydroxyprogesterone, both in a 1% alcoholic solution and in a 1.4% quantity, were used in a night cream with male and female individuals who suffered from high greasiness of the hair, loss of hair and acne vulgaris. The same success was achieved in all cases as was achieved with 11-α-hydroxyprogesterone.

Individual results concerning the cosmetic effects of 11-α-hydroxyprogesterone are summarized in the following tables:

The following symbols mean:
+ =effective; + + =good effect;
+ + + =very good effect; — =not effective;
± =effectiveness in doubt.

TABLE 1

Treatment of Excessive Greasiness of the Hair and of Androgenic Alopecia with 1% 11-α-Hydroxy-Progesterone Solution in 60% Ethanol in Women.

| No. | Age of Person (yrs.) | Treatment Daily Dosage | Duration (months) | Greasiness of Hair | Alopecia | Side Effects |
|---|---|---|---|---|---|---|
| 1 | 45 | 1 × 10 ml | 6 | + | — | hair blunt |
| 2 | 31 | 2 × 10 ml | 5 | ++ | + | none |
| 3 | 17 | 2 × 10 ml | 11 | +++ | + | none |
| 4 | 36 | 2 × 10 ml | 11 | +++ | ++ | none |
| 5 | 40 | 1 × 15 ml | 6 | +++ | ± | none |
| 6 | 40 | 1 × 15 ml | 5 | | + | none |
| 7 | 33 | 1 × 15 ml | 6 | ++ | + | none |
| 8 | 40 | 1 × 15 ml | 5 | + | + | none |
| 9 | 43 | 2 × 10 ml | 12 | +++ | + | none |
| 10 | 24 | 2 × 10 ml | 8 | ± | + | none |
| 11 | 40 | 2 × 10 ml | 9 | ++ | + | none |
| 12 | 27 | 1 × 10 ml | 6 | +++ | + | none |
| 13 | 39 | 2 × 10 ml | 9 | +++ | + | none |
| 14 | 37 | 1 × 15 ml | 4 | +++ | ++ | none |
| 15 | 21 | 1 × 15 ml | 10 | +++ | ++ | none |
| 16 | 44 | 1 × 15 ml | 4 | +++ | | none |
| 17 | 26 | 1 × 15 ml | 4 | ++ | ± | none |
| 18 | 32 | 1 × 10 ml | 1.5 | + | ± | none |

TABLE 2

Treatment of Excessive Greasiness of the Hair and of Androgenic Alopecia with 1% 11-α-Hydroxy-Progesterone Solution in 60% Ethanol in Men.

| No. | Age of Person (yrs.) | Treatment Daily Dosage | Duration (months) | Greasiness of Hair | Alopecia | Side Effects |
|---|---|---|---|---|---|---|
| 1 | 37 | 2 × 12 ml | 11 | +++ | + | none |
| 2 | 24 | 1 × 12 ml | 11 | | + | none |
| 3 | 54 | 1 × 15 ml | 6 | +++ | ++ | none |
| 4 | 27 | 1 × 15 ml | 10 | ++ | + | none |
| 5 | 25 | 1 × 10 ml | 11 | +++ | + | none |
| 6 | 29 | 1 × 10 ml | 11 | +++ | + | none |
| 7 | 33 | 1 × 15 ml | 8 | +++ | ++ | none |
| 8 | 36 | 1 × 15 ml | 3 | ++ | + | none |
| 9 | 35 | 1 × 15 ml | 3 | ++ | + | none |
| 10 | 51 | 1 × 15 ml | 3 | +++ | ± | none |
| 11 | 49 | 1 × 15 ml | 11 | +++ | ++ | none |
| 12 | 37 | 1 × 15 ml | 2 | ++ | ± | none |

TABLE 3

Treatment of Acne Vulgaris With a 1% 11-α-Hydroxyprogesterone Containing, Fatty Night-Cream (Oil-In-Water Emulsion) Which Was Applied in the Customary Manner and Quantity as a Cosmetic.

| No. | Age of Person (yrs.) | Treatment Place | Duration (months) | Acne Vulgaris | Side Effects |
|---|---|---|---|---|---|
| 1 | 43 | face | 7 | +++ | none |
|   |    | upper torso | 7 | +++ | none |
| 2 | 16 | face | 6 | ++ | none |
|   |    | upper torso | 6 | ++ | none |
| 3 | 17 | face | 6 | ++ | none |
|   |    | back | 6 | ++ | none |
| 4 | 36 | face | 5 | +++ | none |
| 5 | 33 | face | 3 | ++ | none |
| 6 | 24 | face | 5 | +++ (*) | none |
| 7 | 39 | face | 5 | ++ | none |
| 8 | 38 | face | 4 | +++ | none |
|   |    | upper torso | 4 | +++ | none |
| 9 | 16 | face | 1.5 | + | none |

(*) The person treated under the current number 6 was dismissed as healed after 5 months of treatment.

In a continued test, the skin of the forehead of two healthy young girls was anointed once daily with 1% solution of 11-α-hydroxyprogesterone in 60% ethanol. Prior to the treatment and on the 14th and 15th day of treatment, the sebaceous content on the skin of the forehead was measured gravimetrically, according to the method of J. S. Strauss and P. E. Pochi, J. Invest. Derm. 36, 293-298 (1961). The results are set forth in Table 4.

TABLE 4

Influencing the Sebaceous Content in the Skin of the Forehead by Treatment with 1% 11-α-Hydroxyprogesterone Solution in 60% Ethanol.

| Individual Subject To Testing | Sebaceous Content in mg/10cm²/3h | | |
|---|---|---|---|
| | Prior to Treatment | On the 14th Day | On the 15th Day |
| Blind Test | 2.54 | | 2.65 |
| A | 3.98 | 3.70 | 1.50 | 1.83 |
| B | 3.13 | 3.20 | 1.80 | 1.90 |

It is clearly seen from Table 4 that the relatively short treatment with 11-α-hydroxyprogesterone results in a definite lowering of the activity of the sebaceous glands. This shows that the active substance of the invention penetrates the skin and produces its effect at the desired place in the skin. These observations are consistent with the results which were obtained in the treatment of excessive greasiness of the hair, of androgenic alopecia and of acne vulgaris. The results of these tests show that 11-α-hydroxyprogesterone used in accordance with this invention is a hair and skin care agent which produces its cosmetic effects especially in the case of androgenically caused disorders of the hair of the head as well as with acne vulgaris by local administration, without any hormonic or other local or general side effects resulting. Therefore, this compound provides a true cosmetic aid.

In accordance with this invention, there are also provided cosmetic hair or skin care compositions. Such compositions contain, in addition to the active substance 11-α-hydroxyprogesterone, additives customarily used in cosmetics. In this way, the active agent of this invention may be present in a hair tonic, a hair oil, a skin oil, a nutritive emulsion for the hair, an aerosol spray, a shampoo, or a dressing agent. Other general or special hair and/or skin care preparations may also contain the active substance in accordance with this invention. The active substance is admixed in these preparations in a quantity which will ensure a reliable effect at regular use. It is preferred to use a concentration of 11-α-hydroxyprogesterone in the range of about 0.5 to 2.0% by weight and, more preferably, 0.8 to 1.4% by weight, based on the total weight of the cosmetic.

The following examples illustrate the use of 11-α-hydroxyprogesterone or one of its pharmaceutically compatible esters in the production of cosmetic hair and skin care agents:

EXAMPLE 1: Production of a Hair Tonic.

| Formulation: | isopropyl alcohol, extra | 52.0 g |
|---|---|---|
| | ethypolyglycol acetate | 2.0 g |
| | 11-α-hydroxyprogesterone | 1.2 g |
| | scented oil | 0.8 g |
| | distilled water | 44.0 g |
| | | 100.0 g |

The active substance, the scented oil and the ethylprolyglycol acetate are mixed with the isopropyl alcohol and the mixture is filled up with water to 100 g.

EXAMPLE 2: Production of a Hair Oil.

| isopropylpalmitate | 30.0 g |
|---|---|
| isopropylmyristate | 20.0 g |
| vaseline oil | 47.0 g |
| 11-α-hydroxyprogesterone | 1.8 g |

-continued

| scented oil | 0.7 g |
|---|---|
| dichlorophone | 0.5 g |
| | 100.0 g |

EXAMPLE 3: Preparation of a Skin Cream.

| almond oil (fat) | 10.0 g |
|---|---|
| cetiol (mixture of esters of unsaturated $C_{12}$-$C_{18}$ fatty acids) | 12.0 g |
| cetyl and stearyl alcohol | 12.0 g |
| Na-salt of the cetyl-stearyl-sulfuric acid ester | 3.0 g |
| glycerine | 6.0 g |
| 11-α-acetoxyprogesterone | 1.4 g |
| scented oil | 0.6 g |
| water | 55.0 g |
| | 100.0 g |

EXAMPLE 4: Production of a Shampoo.

| fatty acid-albumin condensation product ("Lamepon P 60") | 25.0 g |
|---|---|
| glycerine monolaurate-monosulfate | 20.0 g |
| glycerine | 7.0 g |
| 11-α-hydroxyprogesterone | 0.5 g |
| scented oil | 0.5 g |
| water | 47.0 g |
| | 100.0 g |

It is claimed:

1. A cosmetic hair or skin composition selected from the group consisting of a hair cream, a hair oil, a skin cream, a skin oil, an aerosol and a shampoo useful in the treatment of individuals exhibiting excessively greasy hair, androgenic alopecia and/or acne comprising as an active ingredient from about 0.5 to 2.0% by weight based on the total weight of said cosmetic of 11-α-hydroxyprogesterone and/or a pharmaceutically compatible ester thereof in a pharmaceutically acceptable carrier.

2. A composition as defined in claim 1 wherein said cosmetic is a hair cream, or a hair oil.

3. A composition as defined in claim 1 wherein said cosmetic is a skin oil or a nutrient skin cream.

4. A composition as defined in claim 1 in an aerosol spray.

5. A composition as defined in claim 1 in the form of a shampoo.

6. A composition as defined in claim 1 wherein said active ingredient comprises from about 0.8 to 1.4% by weight based on the total weight of said cosmetic.

7. A composition as defined in claim 1 wherein said active ingredient is 11-α-hydroxyprogesterone.

8. A composition as defined in claim 1 wherein said active ingredient is 11-α-acetoxyprogesterone.

9. A method for the treatment of individuals exhibiting acne, or excessively greasy hair which comprises topically treating the affected area with a cosmetic composition containing an effective amount of an active ingredient which is 11-α-hydroxyprogesterone and/or a pharmaceutically compatible ester thereof.

10. A method according to claim 9 in which the condition treated is acne.

11. A method according to claim 9 in which the condition treated is excessive greasiness of the hair.

12. A method as defined in claim 9 wherein said active ingredient is present in a concentration of from about 0.8 to 1.4% by weight based upon the total weight of the cosmetic.

13. A method as defined in claim 9 wherein said active ingredient is 11-α-hydroxyprogesterone.

14. A method as defined in claim 9 wherein said active ingredient is 11-α-acetoxyprogesterone.

15. A method for the treatment of individuals exhibiting androgenic alopecia to reduce hair loss caused by androgenic alopecia, which comprises topically treating the affected area with a cosmetic composition containing an effective amount of an active ingredient which is 11-α-hydroxyprogesterone and/or a pharmaceutically compatible ester thereof.

16. A method as defined in claim 15 wherein said active ingredients is present in a concentration of from about 0.8 to 1.4% by weight based upon the total weight of the cosmetic.

17. A method as defined in claim 15 wherein said active ingredient is 11-α-hydroxyprogesterone.

18. A method as defined in claim 15 wherein said active ingredient is 11-α-acetoxyprogesterone.

* * * * *